United States Patent [19]

Neves

[11] Patent Number: 5,681,534
[45] Date of Patent: Oct. 28, 1997

[54] HIGH THROUGHPUT OLIGONUCLEOTIDE SYNTHESIZER

[76] Inventor: Richard S. Neves, 146 Plain St., Millis, Mass. 02054

[21] Appl. No.: 504,959

[22] Filed: Jul. 20, 1995

[51] Int. Cl.$^6$ .................................................. C08F 2/00
[52] U.S. Cl. .......................... 422/131; 422/62; 422/81; 422/110; 435/91.1; 935/88; 137/561 A
[58] Field of Search ...................... 422/131, 62, 81, 422/110; 435/91.1, 91.2, 91.21, 91.3, 91.31; 536/25.3; 935/16, 17, 88; 137/561 A; 285/131, 150, 155

[56] References Cited

U.S. PATENT DOCUMENTS

| | | | |
|---|---|---|---|
| 3,424,557 | 1/1969 | Skeggs | 422/81 |
| 3,536,450 | 10/1970 | Dus et al. | 422/81 |
| 4,517,338 | 5/1985 | Urdea et al. | 525/54.11 |
| 4,549,567 | 10/1985 | Horton | 137/262 |
| 4,671,941 | 6/1987 | Niina et al. | 422/131 |
| 4,701,304 | 10/1987 | Horn et al. | 422/62 |
| 4,711,268 | 12/1987 | Coleman | 137/597 |
| 5,117,864 | 6/1992 | Byers | 137/561 A |
| 5,156,642 | 10/1992 | Lopez | 137/15 |
| 5,227,224 | 7/1993 | Hutton et al. | 137/597 |
| 5,282,488 | 2/1994 | Roth et al. | 137/15 |
| 5,334,352 | 8/1994 | Johnson | 422/99 |
| 5,387,395 | 2/1995 | Cossain et al. | 422/81 |
| 5,436,143 | 7/1995 | Hyman | 435/91.2 |
| 5,487,569 | 1/1996 | Silvis et al. | 285/24 |
| 5,516,664 | 5/1996 | Hyman | 435/91.52 |
| 5,518,651 | 5/1996 | Reddy et al. | 252/193 |

*Primary Examiner*—Christopher Kim
*Attorney, Agent, or Firm*—Peter A. Borsari

[57] ABSTRACT

The present invention relates to a high-throughput oligonucleotide synthesizer for synthesizing multiple oligonucleotides comprising a pre-existing low throughput oligonucleotide synthesizer which has been integrated with an increased throughput expansion module in order to increase the throughput capacity of the low throughput synthesizer. More specifically, the present invention comprises (a) a pre-existing low-throughput oligonucleotide synthesizer having at least one and no more than eight reactor positions, (b) a plurality of valve manifolds each having a single inlet port and a plurality of outlet ports, (c) a plurality of fluidic connection means each having a first end in fluid connection with one of said reactor positions of the pre-existing low-throughput oligonucleotide synthesizer and a second end in fluidic connection with the inlet port of one of the plurality of valve manifolds and (d) a plurality of reactor positions corresponding in number to the number of valve manifold outlet ports, each of the plurality of reactor positions (d) having a single reactor inlet such that each of said reactor inlets is in fluid connection with a corresponding valve manifold outlet port. Each of the plurality of reactor positions (d) is configured to accept a pre-packaged reactor column, such as a pre-packaged reactor column comprising a substrate having a first 3' base covalently attached thereto. Multiple oligonucleotides are synthesized by the high-throughput oligonucleotide synthesizer of the present invention by the delivery of a stream of reagents from the pre-existing low throughput synthesizer to the plurality of reactor positions (d). In this manner, the high-throughput oligonucleotide synthesizer increases the throughput capacity of a conventional oligonucleotide low throughput synthesizer having the standard 2 or 4 reactor positions to an automated operation of up to 64 reactor positions, and typically from 12 to 24 reactor positions.

17 Claims, 4 Drawing Sheets

HIGH THROUGHPUT OLIGONUCLEOTIDE SYNTHESIZER

FIELD OF THE INVENTION

The present invention relates to oligonucleotide synthesizers and more particularly relates to a device which conveys a pre-existing low-throughput oligonucleotide synthesizer to a high-throughput oligonucleotide synthesizer. The device of the present invention is an expansion module which is integrated with a pre-existing low throughput oligonucleotide synthesizer in order to increase the throughput thereof.

BACKGROUND OF THE INVENTION

In the field of oligonucleotide synthesis, there are several types of synthesizers in use today. For analytical studies, which consume small quantities of oligonucleotides or DNA, either multi-reactor synthesizers or low throughput synthesizers are utilized since these types of synthesizers generate sufficient quantifies of oligonucleotides. The multi-reactor synthesizers are designed to produce numerous oligonucleotides having different sequences on an analytical scale. However, these devices generally are customized instruments having 48 to 96 reactor positions and utilize specialized reactors, such as well, tips or columns and typically are not available commercially. The low throughput synthesizers normally produce from one to eight oligonucleotides while running unattended, each oligonucleotide potentially having a different sequence. The majority of these synthesizers are designed to utilize from one to eight pre-packaged reactor columns which are commercially available from a number of chemical synthesis manufacturers. These pre-packaged reactor columns comprise a substrate carrier having the base of the intended molecule covalently attached thereto. Almost any desired oligonucleotide of any length can be synthesized by the sequential addition of nucleotide monomers (hereinafter sometimes referred to as a "monomer") to the base contained within the pre-packaged reactor column. In other words, the user can synthesize a specific oligonucleotide, such as an oligonucleotide of nineteen base units for immediate analytical testing. As a result, most of the commercially available oligonucleotide synthesizers on the market and in use today are low-throughput synthesizers, generating from one to eight oligonucleotide sequences while running unattended. These low-throughput systems generally synthesize oligonucleotides in one of three modes: parallel, semi-parallel or serial. Parallel mode is the simultaneous synthesis of two or more oligonucleotides. Semi-parallel mode performs some of the chemical process in a parallel mode while other processes are performed in series. A nucleotide synthesizer running in serial mode performs all the required chemical processes of a complete synthesis on each treatment reservoir before proceeding to the other treatment reservoirs.

In the very recent past, commercially available low throughput synthesizers have been developed to perform at a high cycle rate and with low reagent consumption. These latest synthesizers are ideal for use in universities and smaller labs since they are easier and less expensive to operate. A well known example of such a device is the Expedite™, a two reactor column synthesizer manufactured by Perseptive BioSystems. The high cycle rate, which generally provides the addition of one monomer in three to four minutes, allows the user to synthesize a typical oligonucleotide sequence consisting of 30 base units in under two hours. Unfortunately, a serious drawback to these currently available "high cycle" devices is that they utilize a limited number of reactor columns, typically two or four columns. Since most of the desired oligonucleotide sequences used in analytical testing are less than 30 base units and can be synthesized in under two hours, this new generation of low throughput synthesizer cannot be run unattended for any extended period of time. Consequently, the operation of such synthesizers is restricted, such as to an eight hour day, and their high speed cannot be used advantageously for a full 24 hours.

A recent advance in high-throughput synthesizers is disclosed in U.S. Pat. No. 5,288,468 to Church et al. which describes a parallel sequential reactor in which chemical treatment is carried out on a substrate by movement of the substrate from one reagent solution to another. The Church reactor is capable of processing many syntheses in parallel. However, the system is susceptible to cross-contamination of the separate reagents by inefficient washing of the substrate in between reagent changes. Additionally, this reactor utilizes a custom substrate carrier which is not readily obtainable nor is it available as a prepackaged substrate. When a large number of syntheses is desired, the preparation these substrate carriers reduces the throughput effectiveness of the device.

U.S. Pat. No. 5,395,594 to Nokihara et al. describes a device for peptide synthesis, which could be adapted to perform oligonucleotide synthesis. This device can direct a plurality of reagents through needles to a plurality of reactors to perform synthesis in a parallel mode and effectively achieve high throughput. Although the Nokihara synthesizer has the capability to wash the inner and outer surfaces of the needles as they move between reactor positions, thereby effectively minimizing cross-contamination, this device also does not make use of prepackaged reactors. With the large number of synthesis to be performed the process of preparing reactors for this device reduces the effective throughput.

U.S. Pat. No. 5,368,823 to McGraw et al. describes a device which delivers a plurality of reagents to a plurality of reaction columns in a serial mode and removes reagents from the reaction columns in a parallel mode. Although this device is capable of processing many synthesis while unattended, it lacks adequate throughput due to the serial delivery of synthesis reagents. Further, this device does not make use of prepackaged reactors. With the large number of synthesis to be performed the process of preparing reactors for this device reduces the effective throughput.

U.S. Pat. No. 5,324,483 to Cody et al. describes a device that can address many reactors and has environmental control to facilitate the synthesis of many compounds not limited to oligonucleotides. This device does not make use of prepackaged reactors. With the large number of synthesis to be performed the process of preparing reactors for this device reduces its effective throughput.

Despite the teachings of the prior art, a need still exists for a high throughput synthesizer that operates at high cycle rate with low reagent consumption. Additionally, such a device should be capable of taking advantage of the high speed of the reactor and run unattended for several hours. Such a need can be filled by providing an expansion module that increases the throughput of the current high speed low throughput oligonucleotide synthesizers. Such a device should operate with known low-throughput technology and should perform in the same manner as said low-throughput device.

SUMMARY OF THE INVENTION

Accordingly, it is an object of the present invention to provide a device for converting a low-throughput oligonucleotide synthesizer into a high-throughput oligonucleotide synthesizer.

It is another object of the present invention to provide an increased throughput expansion module having a comparable high cycle time as the low-throughput synthesizer.

It is a further object to provide an increased throughput expansion module having comparable low reagent consumption as the low-throughput synthesizer.

It is also an object of the present invention to provide an increased throughput expansion module which is compact in size.

It is still another object of the present invention to provide an increased throughput expansion module which utilizes commercially available prepackaged reactors.

It is a further object of the present invention to provide an increased throughput expansion module which can be run unattended for a number of hours.

It is an additional object of the present invention to provide an increased throughput expansion module that is simple and economical to manufacture.

It is still another object of the present invention to provide an increased throughput expansion module which can be adapted to most high throughput labs and can facilitate high throughput by the way it organizes data and documents operating parameters.

Additional objects, advantages and novel features of the invention will be set forth in part of the description which follows, and in part will become apparent to those skilled in the art upon examination of the following specification or may be learned by practice of the invention.

These and other objects of the invention, as embodied and broadly described herein, are achieved by providing an expansion module comprising fluidic connection means to a pre-existing low-throughput oligonucleotide synthesizer having at least one reactor position and at least one valve manifold having a plurality of outlet ports in fluid connection to a corresponding plurality of reactor positions. Means also may be provided for interfacing the increased throughput expansion module and a pre-existing low-throughput synthesizer to a personal computer.

BRIEF DESCRIPTION OF THE DRAWINGS

The present invention will be better understood with reference to the appended drawing sheets, wherein.

DETAILED DESCRIPTION

The present invention relates to an expansion module for increasing the throughput capability of a pre-existing low-throughput oligonucleotide synthesizer. The Increased Throughput Expansion Module (hereinafter sometimes referred to as the expansion module or simply the ITEM) comprises the following elements:

(a) fluidic connection means to a low-throughput synthesizer having at least one reactor position;

(b) at least one valve manifold; and (c) a plurality of reactor column positions, each position comprising (1) a reactor inlet for receiving fluid from said valve manifold and (2) a reactor outlet for discharging effluent from said reactor position to a waste reservoir. In a preferred embodiment, the expansion module further comprises:

(d) a waste reservoir for receiving said discharged fluid; and (e) means for interfacing said increased throughput expansion module and said low throughput synthesizer to a personal computer.

Figure 1:
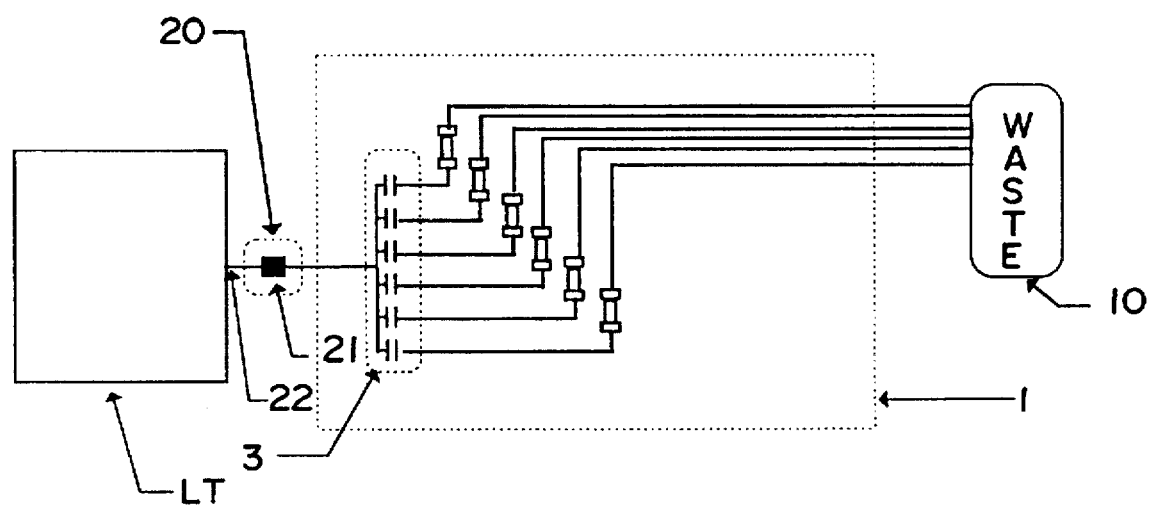
FIG. 1 shows a fluidic schematic view of the increased throughput expansion module the present invention integrated with a pre-existing low-throughput oligonucleotide synthesizer.
Figures 2, 2A:
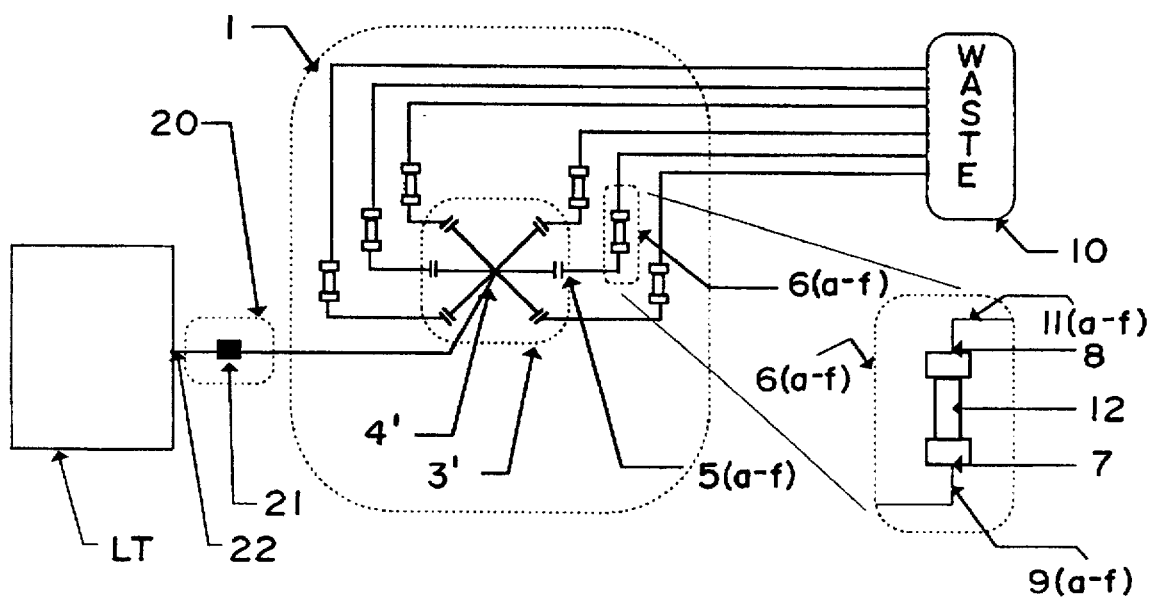
FIG. 2 shows a fluidic schematic view of an alternate embodiment of the present invention integrated with a pre-existing low-throughput oligonucleotide synthesizer.

Referring to FIGS. 1 and 2, the increased throughput expansion module 1 comprises a fluidic connection means 20 for fluidic interface with a pre-existing low-throughput oligonucleotide synthesizer LT as described below, a valve manifold 3 having an inlet port 4 and a plurality of outlet ports 5, a plurality of reactor column positions 6, each position comprising a reactor inlet 7 and a reactor outlet 8, a waste reservoir 10 and means for interfacing the increased throughput expansion module 1 and the pre-existing low-throughput oligonucleotide synthesizer LT to a personal computer. In the embodiment shown in FIGS. 1 and 2, six outlet ports 5a to 5f are depicted; however, it is to be understood that the valve manifold can be configured with any number of outlet ports, the number of outlet ports being restricted only to maintain a minimal internal volume of the valve manifold as to not diminish synthesis performance. Similarly, although six reactor column positions 6a to 6f are depicted, it is to be understood that the number of reactor column positions can be increased in correlation with the number of outlet ports 5 of the valve manifold.

Each reactor column position is fashioned to receive a pre-packaged reactor column 12, hereinafter sometimes referred to as reactor columns or simply columns. The pre-packaged reactor columns 12 are standard, commercially available reactor columns for oligonucleotide synthesis manufactured by a variety of chemical providers, such as Prime Synthesis and Perseptive BioSystems, Inc. These pre-packaged reactor columns are provided with a substrate having a first 3' base covalently attached thereto.

The valve inlet 4 receives fluid containing a stream of reagents from the low-throughput synthesizer LT to the valve manifold 3 which is in fluidic interface with the reactor columns 12 through lines 9. More specifically, as shown in FIG. 2, fluid is directed from the outlet ports 5a to 5f through lines 9a to 9f respectively and to the reactor column inlets 7a to 7f, respectively. Effluent from the reaction is discharged from the reactor column outlets 8 (specifically, column outlets 8a to 8f) to waste reservoir 10 through lines 11 (e.g. 11a to 11f).

As shown in FIGS. 1 and 2, the expansion module interfaces by fluid communication with the reactor inlet of the pre-existing low-throughput synthesizer LT. More particularly, the expansion module 1 is fluidly connected with the synthesizer LT by means of an interconnect 20. Interconnect 20 comprises a coupling unit 21 having a first end attached to the inlet 22 of a reactor position of the low-throughput synthesizer, and a second end fluidly connected to inlet port 4 by fluid tubing. As will be recognized by skilled practitioners, such interconnecting means are well known in the art. However, in order to attain high-quality synthesis, it is important that the interconnect 20 between the pre-existing low-throughput oligonucleotide synthesizer and the present expansion module produces a zero dead volume attachment.

The pre-existing low-throughput synthesizer LT shown in the FIGS. 1 and 2 accommodates one pre-packaged reactor column (not shown) at the reaction position having a reactor inlet 22. In normal operation, the low-throughput synthesizer is programmed to cause a stream of reagents to flow through the column inlet, said stream containing the necessary reagents for the elongation of the oligonucleotide molecule covalently attached to a support contained in the reactor column. The stream of reagents is delivered to the column inlet in a series of cycles, each cycle including, for example, a deblocking step to remove the 5' protecting group, a coupling step to elongate the oligonucleotide chain (e.g. the addition of a nucleotide base), and a post coupling step which includes capping unreacted chains and oxidizing the phosphorous atom. In other words, the oligonucleotide is elongated by one base by every cycle. The assemblage of cycles, the quantity of the stream of reagents and the effective residence time presented to the reactor column are commonly referred to as the protocol, which has been optimized by the low-throughput synthesizer manufacturer in order to produce the highest quality oligonucleotide sequence for each reactor column.

In the present invention, the pre-existing low throughput synthesizer is not loaded with pre-packaged reactor column. Rather, the low throughput synthesizer's reactor inlet 22 is fluidly connected to valve inlet port 4 and delivers the stream of reagents to the valve manifold 3. The stream of reagents is directed from the outlet ports 5a to 5f through lines 9a to 9f respectively, and to the reactor column inlets 7a to 7f respectively for elongation of the oligonucleotide molecules in the reactor columns 12. In this manner, the throughput capacity of the low throughput synthesizer has been increased from six fold (that is, from one reactor to six reactors).

The diversion of the stream of reagents through the expansion module's valve manifold necessitates the modification of the protocol in order to optimize it for use with the present expansion module. This modification of the protocol is accomplished by the addition of an offset. The offset functions to adjust the protocol such that optimal residence time occurs at the reactor positions within the expansion module. The protocol is further modified by addition of washing steps to account for the reduction of washing effectiveness due to dilution of the stream.

The valve manifold 3 shown in FIG. 1 is a linear configuration. The use of a linear manifold provides a continuous flow path for the stream of reagents and also facilitates optimal washing. However, the linear manifold requires a different offset adjustment for every reactor position fed by the manifold due to the varying volumes between the inlet port 4 and the several reactor positions. In the alternate embodiment shown in FIG. 2, a valve manifold 3' having a radial configuration is employed, instead of the linear manifold 3 depicted in FIG. 1. An advantage of the radial manifold 3' is that the volume between the inlet port 4' and the several reactor positions is equal. Therefore, the device is able to make use of a single protocol for all reactor positions fed by the manifold.

Figure 3:
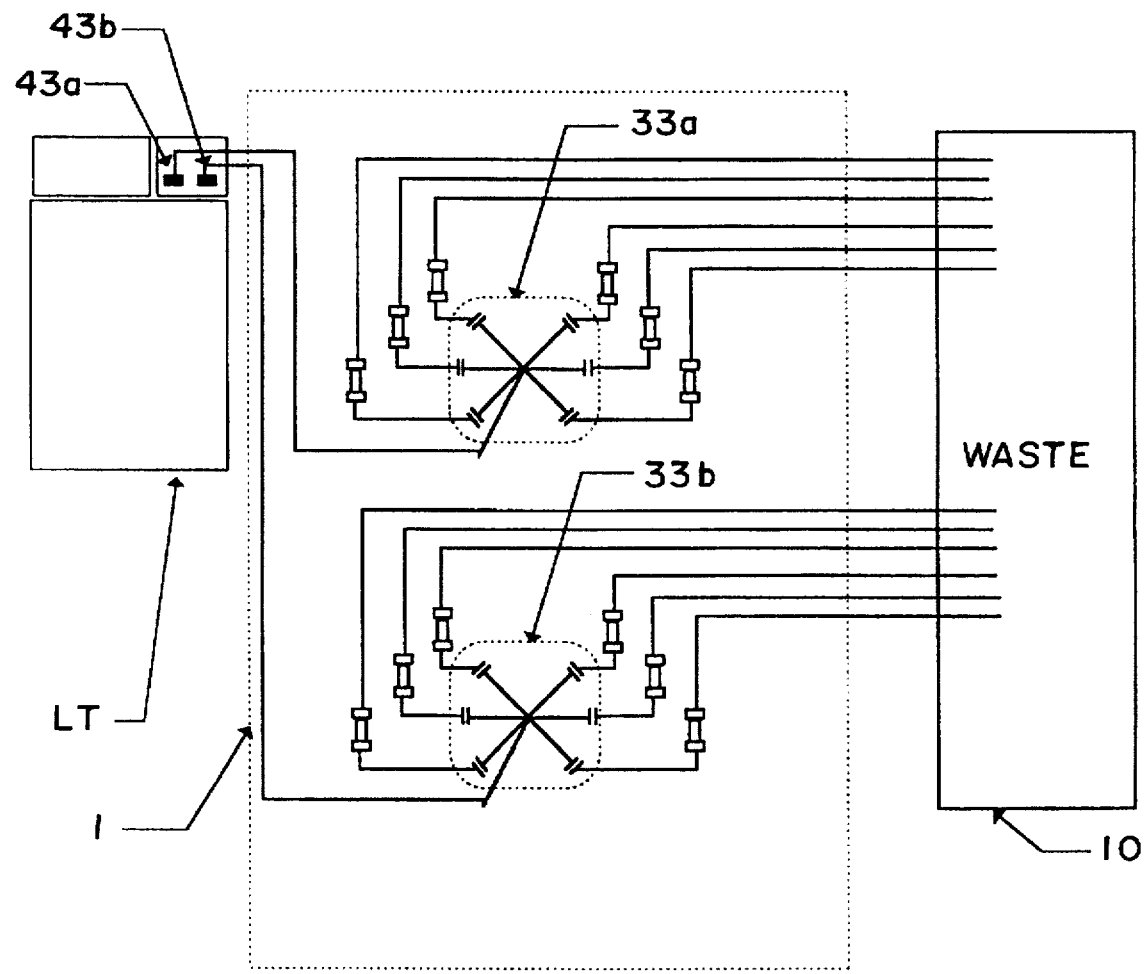
FIG. 3 shows a fluidic schematic view of the present invention integrated with a pre-existing low-throughput oligonucleotide synthesizer having two reactor columns.

The increased throughput expansion module of the present invention comprises at least one valve manifold 3. Preferably the number of valve manifolds provided in the expansion module equals the number of reactor positions provided in the pre-existing low throughput oligonucleotide synthesizer. For example, for integration with a pre-existing low throughput synthesizer having four reactor positions, the expansion module is equipped with four valve manifolds. As shown in FIG. 3, the pre-existing low throughput synthesizer contains two reactor positions 43a and 43b and is integrated with an expansion module of the present invention have two valve manifolds 33a and 33b respectively. More particularly, valve manifold 33a is fluidly connected to reactor position 43a and valve manifold 33b is fluidly connected to reactor position 43b. In this manner, the number of reactor positions have been expanded from two to twelve, thereby increasing the throughput capacity of the synthesizer by six fold.

Figure 4:
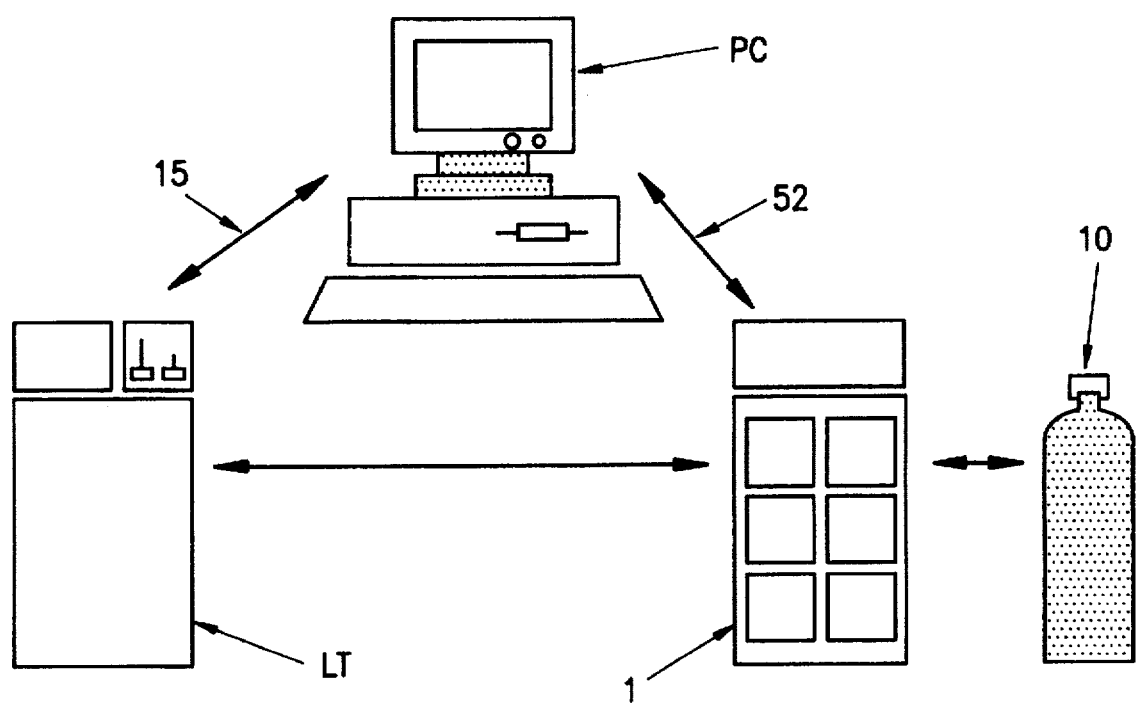
FIG. 4 shows a diagram detailing the control connections between the increased throughput expansion module of the present invention and the pre-existing low throughput oligonucleotide synthesizer interfacing with a personal computer.

In a preferred embodiment, the expansion module is provided with means for computer interfacing with the pre-existing low-throughput synthesizer. Referring to FIG. 4, control and fluidic interface connections are provided between the present expansion module 1 and the pre-existing low throughput synthesizer LT. In this embodiment, a personal computer PC controls the high level operation of the synthesizer LT through an interface cable 51. This high level operation comprises the submitting of synthesis jobs and the monitoring of the sequence progression, as well as detecting any fault conditions. The personal computer interface with the expansion module 1 through interface cable 52 controls the operation of the valve manifolds and coordinates the manifolds with the synthesis jobs being sent through the synthesizer LT.

While particular embodiments of the invention have been described, it will be understood, of course, that the invention is not limited thereto, and that many obvious modifications and variations can be made, and that such modifications and variations are intended to fall within the scope of the appended claims.

What is claimed is:

1. A high-throughput oligonucleotide synthesizer for synthesizing multiple oligonucleotides comprising:
   (a) a pre-existing low-throughput oligonucleotide synthesizer having no more than eight reactor positions;
   (b) a plurality of valve manifolds, each of said valve manifolds having (1) a single inlet port and (2) a plurality of outlet ports;
   (c) a plurality of fluidic connection means, said plurality of fluidic connection means being equal to the number of reactor positions of said pre-existing low-throughput oligonucleotide synthesizer, each of said fluidic connection means having a first end in fluid connection with one of said reactor positions of said pre-existing low-throughput synthesizer and a second end in fluidic connection with one of said inlet ports of said plurality of valve manifolds, such that each of said plurality of valve manifolds is in fluidic connection with one of said reactor positions of said pre-existing low-throughput oligonucleotide synthesizer; and
   (d) a plurality of reactor positions corresponding in number to said plurality of outlet ports of said plurality of valve manifolds, each of said plurality of reactor positions comprising a single reactor inlet and a single reactor outlet and being capable of receiving a reactor column, such that each reactor inlet of said plurality of reactor positions is in fluidic connection with a corresponding valve manifold outlet port;

whereby the throughput capacity of the pre-existing low-throughput oligonucleotide synthesizer is multiplied by the number of plurality of outlet ports of said plurality of valve manifolds.

2. The high-throughput oligonucleotide synthesizer in accordance with claim 1, wherein each of said plurality of fluidic connection means is in the form of an interconnect comprising a coupling unit having a first end attached to the inlet of said reactor position of said pre-existing low throughput synthesizer and having a second end connected by tubing means to said inlet port of one of said plurality of valve manifolds, said interconnect being configured in such a manner as to produce a zero dead volume attachment.

3. The high-throughput oligonucleotide synthesizer in accordance with claim 1, wherein each of said plurality of valve manifolds comprises six outlet ports.

4. The high-throughput oligonucleotide synthesizer in accordance with claim 1, wherein said pre-existing low-throughput oligonucleotide synthesizer comprises from two to four reactor positions.

5. The high-throughput oligonucleotide synthesizer in accordance with claim 4, wherein each of said plurality of valve manifolds comprises at least four outlet ports.

6. The high-throughput oligonucleotide synthesizer in accordance with claim 1, further comprising (e) a waste reservoir for receiving discharged effluent from said reactor outlets of said reactor positions (d).

7. The high-throughput oligonucleotide synthesizer in accordance with claim 1, further comprising (f) means for interfacing to a personal computer.

8. The high-throughput oligonucleotide synthesizer in accordance with claim 1, wherein each of said plurality of valve manifolds has a linear configuration.

9. The high-throughput oligonucleotide synthesizer in accordance with claim 1, wherein each of said plurality of valve manifolds has a radial configuration.

10. The high-throughput oligonucleotide synthesizer in accordance with claim 1, wherein each of said plurality of reactor positions (d) is configured to accept a pre-packaged reactor column.

11. The high-throughput oligonucleotide synthesizer in accordance with claim 10, wherein said pre-packaged reactor column comprises a substrate having a first 3' base covalently attached thereto.

12. The high-throughput oligonucleotide synthesizer in accordance with claim 1, wherein said multiple oligonucleotides are synthesized by the delivery of a stream of reagents from said reactor position of said low-throughput oligonucleotide synthesizer to said reactor inlet of each of said plurality of said reactor positions (d).

13. The high-throughput oligonucleotide synthesizer in accordance with claim 12, wherein each of said reactor positions (d) contains a pre-packaged reactor column.

14. A high-throughput oligonucleotide synthesizer for synthesizing multiple oligonucleotides comprising:

(a) a pre-existing low-throughput oligonucleotide synthesizer having two reactor positions;

(b) two radial valve manifolds, each of said valve manifolds having (1) a single inlet port and (2) a plurality of outlet ports;

(c) two fluidic connection means, each of said fluidic connection means having a first end in fluid connection with one of said reactor positions of said pre-existing low-throughput synthesizer and a second end in fluidic connection with one of said inlet ports of said valve manifolds, such that each valve manifold is in fluidic connection with one of said reactor positions of said pre-existing low-throughput oligonucleotide synthesizer; and (d) a plurality of reactor positions corresponding in number to said plurality of outlet ports of said two valve manifolds, each of said plurality of reactor positions comprising a single reactor inlet and a single reactor outlet and being capable of receiving a reactor column, such that each reactor inlet of said plurality of reactor positions is in fluidic connection with a corresponding valve manifold outlet port;

whereby the throughput capacity of the pre-existing low-throughput oligonucleotide synthesizer is multiplied by the number of plurality of outlet ports of said plurality of valve manifolds.

15. The high-throughput oligonucleotide synthesizer in accordance with claim 14, wherein each of said fluidic connection means is in the form of an interconnect comprising a coupling unit having a first end attached to the inlet of said reactor position of said pre-existing low throughput synthesizer and having a second end connected by tubing means to said inlet port of one of said of valve manifolds, said interconnect being configured in such a manner as to produce a zero dead volume attachment.

16. The high-throughput oligonucleotide synthesizer in accordance with claim 15, wherein each valve manifold comprises six outlet ports, each of said outlet ports being in fluidic connection with a corresponding reactor inlet of said plurality of reactor positions (d).

17. The high-throughput oligonucleotide synthesizer in accordance with claim 14, wherein each of said plurality of reactor positions (d) is configured to accept a pre-packaged reactor column comprising a substrate having a first 3' base covalently attached thereto, such that multiple oligonucleotides are synthesized by the delivery of a stream of reagents from each of the reactor inlets positions of said low throughput synthesizer to each of said reactor inlets of said plurality of reactor positions (d).

* * * * *